June 26, 1934. E. H. SCHULTZ ET AL Plant Pat. 99
HYBRID BARBERRY
Filed March 23, 1933
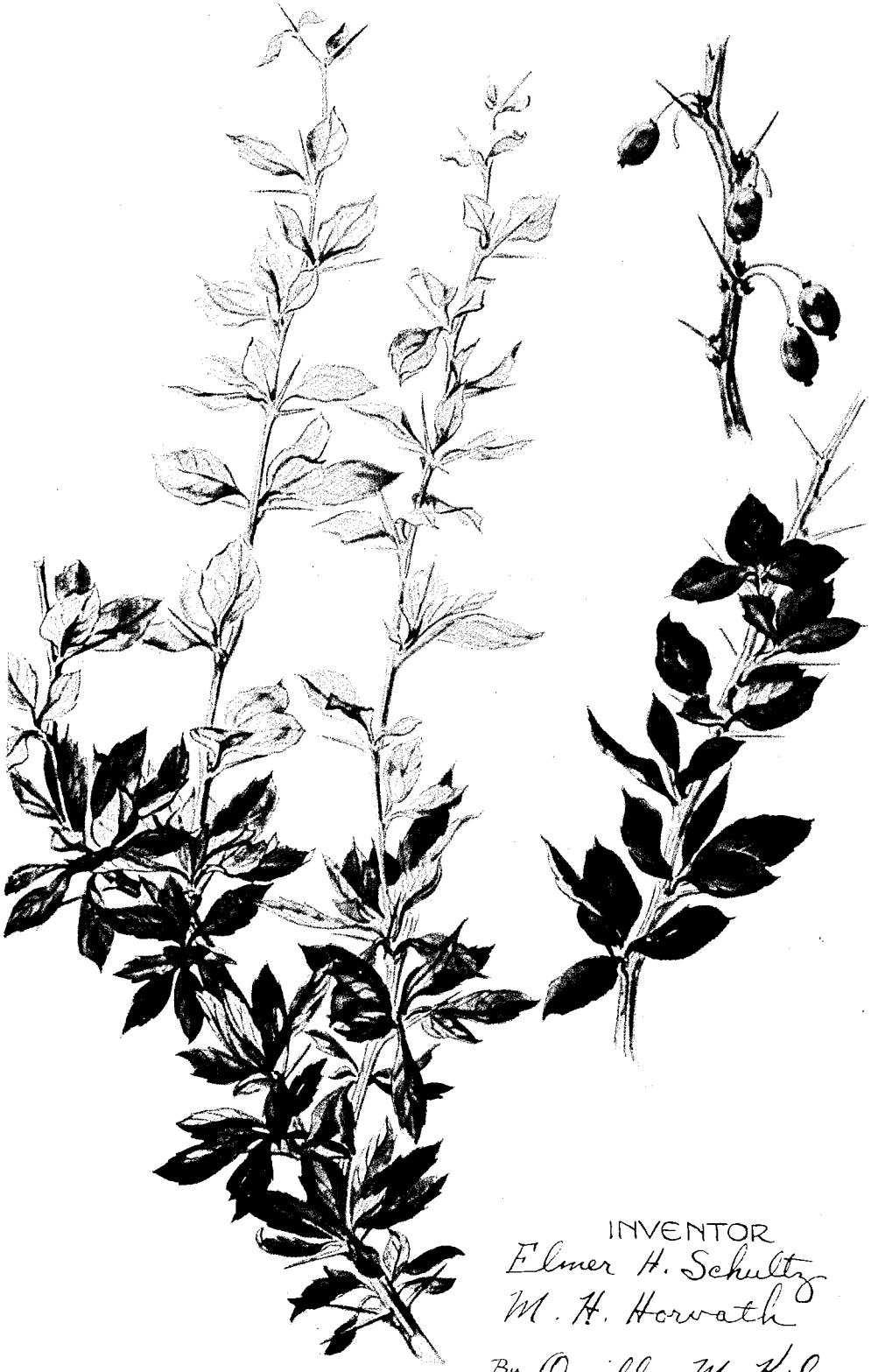
INVENTOR
Elmer H. Schultz
M. H. Horvath
By Orville M. Kile
PLANT PATENT AGENT Patented June 26, 1934

UNITED STATES PATENT OFFICE

99

HYBRID BARBERRY

Elmer H. Schultz and Michael Henry Horvath, Mentor, Ohio, assignors to Wayside Gardens Company, Mentor, Ohio Application March 23, 1933, Serial No. 662,358

1 Claim. (Cl. 47—59)

Our present invention relates to improvements in barberry plants of the type suitable for ornamental use.

Our new barberry is the product of definite scientific plant breeding work carried on by ourselves, and resulted from the crossing of *Berberis thunbergi* and *Berberis juliana*. This new hybrid may be described broadly as possessing the principal virtues of *B. thunbergi*—vigorous growth, freedom from rust, and extreme hardiness—together with the beautiful semi-evergreen to evergreen leaves of *B. juliana*. This new variety has amply proved its ability to reproduce asexually, but has not yet been introduced to the public.

The accompanying illustrations show in full color and approximately natural size (1) a branch of one-year-old wood with the newer lighter green current season's growth—cut about June 20, (2) a section of branch cut about January 10, showing the typical late fall and winter foliage of reddish brown, and (3) a section of branch showing the berries or seed bodies, cut about November 10. All dates refer to conditions of the plant in the vicinity of northern Ohio at the time specified.

The following is a detailed description of this new hybrid barberry.

*Habits of growth.*—Vigorous, healthy bush 5 to 6 feet high, branches spreading like *B. thunbergi*, old stems angular and brown to dark brown, perfectly hardy in northern Ohio, rapid growth, easily propagated.

*Foliage.*—Each plant bears summer foliage of two decidedly different types—that on the branches of the new or current season's growth and that on the older branches. The leaves on the new growth are relatively large and inclined to the spatulate form, being about 1¼ inches long and ¾ inches wide in late June, in the latitude of northern Ohio, on those portions of the new branch which represent the more mature part of the current season's growth. At the same time and place the larger leaves on the branches one year old or more measure approximately 1½ inches long by ½ inch wide, thus being much longer and narrower in shape.

The leaves on the older growth are arranged in groups or clusters arising from nodes from which also arise the thorns. The leaves growing in these clusters may vary in number from seven to ten and are of notably different lengths.

The leaves on the new growth are light green in color while those on the previous year's growth are dark green. In rather wet seasons these leaves remain dark green throughout the fall and, in the latitude of northern Ohio, until late January or February. They then change to a rich brownish red color. During late March this foliage largely drops off and early in April the new leaves appear. In more southerly latitudes, however, the old foliage remains dark green throughout the year and does not drop off except for a slow shedding of the older leaves and replacement with new ones. This "shedding" is most pronounced in the summer after a considerable growth of new leaves has been attained. In seasons when the fall months are rather dry the foliage changes color earlier and some of the tip leaves may become reddish brown in November (in the latitude of northern Ohio).

The leaves on the older growth are almost entire but have a few very small barbs or hair-like projections on their edges—one at the extreme tip of each leaf and one to three or four on each edge of the leaf grouped about half way between apex and base.

The leaf and thorn arrangement of this new variety is similar to that of *B. juliana*, also the shape and size of leaves. But the upper surfaces and edges of the leaves are quite different from those found in *B. juliana*. *B. juliana* is deeply veined and has large and very sharp teeth on edges.

The young leaves on *B. juliana* do not have the broad short effect found in this new variety.

The thorns are a prominent feature, being about ½ inch long and in three parts on the older growth, approximately the same as in *Berberis bulgaris*. On the newer growth thorns are generally single or with a rudimentary prong at the base.

Blossoms are bright yellow, small and occur singly. This variety blooms very sparsely.

Fruits are dull red to purplish red, elongated and occur on single stems arising from the axils of the leaves; seldom more than two stems arising from the same leaf axil. Only a few fruits are found, ordinarily, on each plant.

Having thus fully disclosed our invention we claim:

The variety of barberry plant herein shown and described, characterized particularly by the vigorous growth, freedom from rust and extreme hardiness found in *B. thunbergi*, combined with semi-evergreen to evergreen foliage.

M. H. HORVATH.
ELMER H. SCHULTZ.